United States Patent [19]

Maass et al.

[11] 4,060,537
[45] Nov. 29, 1977

[54] PREPARATION OF ORGANOSILOXANES

[75] Inventors: Günther Maass, Cologne; Hans Joachim Lücking; Werner Büchner, both of Leverkusen; Bruno Degen, Schildgen, all of Germany

[73] Assignee: Bayer Aktiengesellschaft, Leverkusen, Germany

[21] Appl. No.: 747,262

[22] Filed: Dec. 3, 1976

[30] Foreign Application Priority Data

Dec. 20, 1975 Germany .............................. 2557624

[51] Int. Cl.² .............................................. C07F 7/08
[52] U.S. Cl. .............................................. 260/448.2 E
[58] Field of Search .................................. 260/448.2 E

[56] References Cited

U.S. PATENT DOCUMENTS 3,546,265  12/1970  Schank ..................... 260/448.2 E
3,803,195   4/1974  Nitzsche et al. ............ 260/448.2 E

OTHER PUBLICATIONS

"Chem. Ber.", 97, p. 1069 (1964).

Primary Examiner—Paul F. Shaver
Attorney, Agent, or Firm—Burgess, Dinklage & Sprung

[57] ABSTRACT

In the preparation of cyclic and linear organosiloxanes by reacting an organohalogenosilane with a compound of the formula

ROR' in which

R is an alkyl radical with 1–4 C atoms, and
R' is hydrogen or an alkyl radical with 1–4 C atoms, the improvement which comprises effecting the reaction in an aqueous solution of a Lewis acid. Preferably the organohalogenosilane is a di- or tri-organo-chloro or -bromo-silane wherein the organo radical is selected from the group consisting of alkyl or alkenyl of up to 4 C atoms or aryl, especially dimethyldichlorosilane, and the Lewis acid is a 40–90% solution of $ZnCl_2$, $FeCl_3$, $CdCl_2$ or $H_2SO_4$. Advantageously ROR' is methanol, ethanol, propanol, dimethyl ether or diethyl ether.

6 Claims, No Drawings

PREPARATION OF ORGANOSILOXANES

The present invention relates to a process for the preparation of organosiloxanes, with simultaneous formation of alkyl halides, by reaction of alkylhalogenosilanes with alcohols or ethers in an aqueous solution of a Lewis acid.

Many organosiloxanes, and especially compounds of the general formula

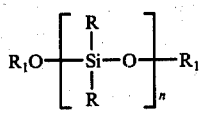

in which
R can represent, for example, an aryl radical or an alkyl radical with 1-4 C atoms,
n can assume numbers between 0 and several hundred and
$R_1$ denotes trialkylsilyl (alkyl = methyl, ethyl, propyl or butyl) or hydrogen,
and also cyclic siloxanes of the formula

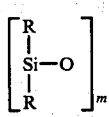

in which
m is greater than 2 and in particular is 3 or 4, are prepared by hydrolysis of the corresponding organohalogenosilanes. The dimethylsiloxanes, which are producible by hydrolysis of dimethyldichlorosilane, are, above all, of particular importance industrially. In addition to the technical difficulties relating to the material, which are incurred with this exothermic process, it is, above all, the disposal or working up of the amounts of dilute hydrochloric acid which are obtained which presents serious problems which it has not yet been possible to solve satisfactorily.

In order to eliminate this disadvantage, it has already been proposed in U.S. Pat. No. 2,741,630 to carry out an alcoholysis in place of the hydrolysis mentioned, an alkyl chloride corresponding to the alcohol employed being formed in this case instead of hydrochloric acid. The problem of the waste hydrochloric acid can be solved in this way and the alkyl chloride which now results can be re-used in the preparation of alkylchlorosilanes. However, the main disadvantage of the processes which operate in accordance with this principle and were known hitherto is that the quality of the resulting siloxane is unsatisfactory.

A process in which dimethyldichlorosilane and methanol are fed into a salt melt consisting of zinc chloride and potassium chloride at temperatures between 300° and 350° C has also been disclosed in Chem. Ber. 97, 1,069 (1964). With this process, dimethylsiloxanes, methyl chloride and water are formed. However, this reaction does not proceed to completion and siloxanes which still carry terminal chlorine atoms are obtained. In addition, Si—C bonds are split at the high temperatures prevailing during this process, so that the mixture of siloxanes formed can no longer be employed as the starting material for homogeneous linear polymers.

It is known from U.S. Pat. No. 2,741,630 to react methanol and dimethyldichlorosilane in the vapor state at temperatures of about 300° C on $SiO_2$ beads which are charged with zinc chloride. The problem of SiC splitting arises with this process also and, moreover, the surface of the $SiO_2$ beads becomes inactive after a short time due to deposits of high-molecular siloxanes and scission products.

In order to prevent the splitting of Si—C bonds, it has also already been proposed to react dimethyldichlorosilane and methanol at lower temperatures. Thus, for example, in U.S. Pat. No. 2,556,897 a process is described in which methanol and dimethyldichlorosilane are reacted in order to prepare polydimethylsiloxanes and methyl chloride. The reaction is carried out at 40°-60° C using a 100% excess of methanol. However, the reaction times required for the conversion are so long that this process cannot be considered for use on a large industrial scale. A further disadvantage of this process is that the methanol employed must be anhydrous.

The process according to German Offenlegungsschrift (German Published Specification) No. 2,148,669 therefore makes use of a reactor filled with active charcoal for the reaction of methanol and dimethylchlorosilane. However, in industrial operation the active charcoal crumbles and contaminates the apparatuses, and the polydimethylsiloxanes formed, with extremely fine carbon dust which can be removed again only with great effort. Moreover, the proportion of cyclic siloxanes formed during this process is very small. It is precisely these cyclic siloxanes, and especially octamethylcyclotetrasiloxane, which are particularly valuable, since they can be employed as defined starting substances for further reactions. Efforts are therefore being made to obtain as high a proportion as possible of these cyclic compounds from the preparation of siloxanes.

The subject of the present invention is, now, a process for the preparation of linear and cyclic organosiloxanes by reaction of organohalogenosilanes with compounds of the general formula ROR', in which
R represents an alkyl radical with 1-4 C atoms and
R' represents hydrogen or an alkyl radical with 1 - 4 C-atoms
which is characterized in that the reaction of the organohalogenosilane with ROR' is carried out in an aqueous solution of a Lewis acid.

Surprisingly, it has been found that the process according to the invention gives very good yields of siloxanes, and especially cyclic siloxanes, at relatively low temperatures and with short reaction times. The fact that the proportion of cyclic siloxanes which is formed is so high, and can be up to 95%, is particularly surprising since it is known (from, for example, Noll, Chemie und Technologie der Silicone (Chemistry and Technology of Silicones), 1968, page 189) that Lewis acids act as polymerization catalysts on low-molecular, cyclic siloxanes.

Suitable starting materials for the process according to the invention are, in particular, diorganodihalogenosilanes or triorganohalogenosilanes in which lower alkyl or alkenyl groups containing up to 4 C-atoms or aryl groups, such as, for example, methyl, ethyl, vinyl, phenyl and the like, are present as the organic radicals. Chlorine and bromine are possible as the halogen in these types of compound. The organochlorosilanes are preferred. When organobromosilanes are employed, the corresponding alkyl bromides are formed. Mixtures of different organochlorosilanes can also be employed. Examples of preferred compounds are dimethyldichlorosilane, trimethylchlorosilane and divinyldichlorosilane.

Lower alcohols, such as, for example, methanol, ethanol or propanol, serve as the reactants and amongst these alcohols methanol is particularly preferred since it gives methyl chloride, which is important for the preparation of methylchlorosilanes. Since the reaction is carried out in an aqueous solution of a catalyst, mixtures of alcohol and water can also be employed. Ethers, such as, for example, dimethyl ether or diethyl ether, can also be used in place of alcohols for the reaction with the organohalogenosilane. The molar ratio of the methyl group in the alcohol or ether to the Si—Cl group should be about 1:1 to 1.5:1.

An aqueous solution of a Lewis acid, such as, for example, $ZnCl_2$, $FeCl_3$, $CdCl_2$ or $H_2SO_4$, serves as the reaction medium. Amongst these acids, $ZnCl_2$ is preferably employed. The concentration of the aqueous solution of the acid depends on the temperature employed and this varies between about 120° and 190° C under normal pressure, but under excess pressure or reduced pressure can be changed correspondingly.

A concentration of about 40 to 90% by weight of Lewis acid in the aqueous solution is preferably employed.

In the case of the preferred use of the process according to the invention for the reaction of methanol with dimethyldichlorosilane, the reaction is appropriately carried out at temperatures between about 130° and 180° C, preferably about 140°–170° C. The volatile constituents consisting of cyclic siloxanes, such as hexamethylcyclotrisiloxane, octamethyl-cyclotetrasiloxane or decamethylpentasiloxane, make up about 95% of the theoretical yield at 150° C and, after cooling the reaction products, are separated from the aqueous phase which is formed at the same time. The non-volatile constituent of the siloxanes is separated from the aqueous solution of the catalyst. Impurities of, for example, the hydrolysis products of methyltrichlorosilane, which can very easily be contained in dimethyldichlorosilane, collect in the nonvolatile constituent of the siloxanes and the bulk of the siloxane is thus freed from trifunctional siloxy units. This additional effect of purifying the siloxane is a further advantage of the process.

The siloxanes formed are used as intermediate products for the preparation of silicone oils of very diverse composition, silicone rubber and other silicone polymers. The alkyl halides are also intended for further processing and in particular the methyl chloride which can be prepared according to the process is used to synthesize methylchlorosilanes by the Rochov method. The process is highly advantageous, particularly because it is not harmful to the environment.

The process according to the invention will now be illustrated in even more detail with the aid of the examples which follow:

EXAMPLE 1

The reaction of dimethyldichlorosilane and methanol was carried out at about 155° C in a bubble column which was 110 cm long, had a diameter of 6.5 cm and was filled with an approximately 81% strength aqueous solution of zinc chloride. The base was designed as a frit and a second frit 3 cm in diameter was fitted 4 cm above this. A foam-breaking sphere with a gas outlet, which was connected to a descending cooler by means of tubing, was fitted on the upper end of the column. This water cooler was located on a 2 l two-necked flask. An ascending cooler, which was operated at −10° C, was fitted into the second ground joint of the flask. Tubing passed from the upper end of this cooler into a trap which was cooled with methanol/solid carbon dioxide. 130 g of dimethyldichlorosilane were pumped per hour through the base frit and 90 g of methanol were pumped per hour into the reactor through the upper frit. After they had been condensed in the two-necked flask, the gaseous, hot reaction products gave, per hour, 72 g of siloxanes (consisting to the extent of 71% by weight of octamethylcyclotetrasiloxane) with a viscosity of 3.5 cP and 36 g of methanol-containing hydrochloric acid (3.7 g of HCl). 111 g of a mixture of 13% by weight of dimethyl ether and 87% by weight of methyl chloride collected in the solid carbon dioxide trap. At the end of the experiment, a layer of siloxane had formed on top of the zinc chloride solution. About 2 g of this highly viscous silicone oil had formed per hour. The yield of methyl chloride was 95% and that of readily volatile cyclic siloxanes was about 98%.

EXAMPLE 2

128 g of dimethyldichlorosilane and a mixture of 65 g of methanol and 62 g of water were reacted, per hour, in the apparatus used in Example 1 and in the manner described in that example. 73 g of siloxanes with a viscosity of 2.3 cP, 95 g of a hydrochloric acid/methanol mixture and 89 g of a mixture of 3.5% of dimethyl ether and 96.5% of methyl chloride formed per hour. In addition, 1 g of non-volatile siloxane had formed per hour. The yield of hexamethylcyclotrisiloxane, octamethylcyclotetrasiloxane and decamethylcyclopentasiloxane was, in total, about 93%. The yield of methyl chloride was 85%.

EXAMPLE 3

The apparatus used in Example 1 was also used for a reaction of trimethylmonochlorosilane with methanol. 65 g of methanol and 140 g of trimethylmonochlorosilane were reacted per hour. The yield of hexamethyldisiloxane was 104 g (100%) and that of methyl chloride was 62 g (95%). In addition, 3 g of dimethyl ether and 35 g of a methanol/hydrochloric acid mixture containing 60% of methanol and 5.3% of hydrogen chloride were obtained.

It will be appreciated that the instant specification and examples are set forth by way of illustration and not limitation, and that various modifications and changes may be made without departing from the spirit and scope of the present invention.

What is claimed is:

1. In the preparation of cyclic and linear organosiloxanes by reacting an organohalogenosilane with a compound of the formula

ROR' in which
  R is an alkyl radical with 1–4 C atoms, and
  R' is hydrogen or an alkyl radical with 1–4 C atoms, the improvement which comprises effecting the reaction in an aqueous solution of a Lewis acid.

2. The process according to claim 1, wherein the organohalogenosilane is a di- or tri-organo-chloro- or bromosilane wherein the organo radical is selected from the group consisting of alkyl or alkenyl of up to 4 C atoms or aryl and the Lewis acid is employed in a concentration of about 40 to 90%.

3. The process according to claim 2, wherein the organo radical is selected from the group consisting of methyl, ethyl, vinyl and phenyl, the halogeno radical is chloro, ROR' is selected from the group consisting of methanol, ethanol, propanol, dimethyl ether and diethyl ether, and the Lewis acid is selected from the group consisting of $ZnCl_2$, $FeCl_3$, $CdCl_2$ and $H_2SO_4$.

4. The process according to claim 1, wherein $ZnCl_2$ is employed as the Lewis acid.

5. The process according to claim 1, wherein dimethyldichlorosilane is employed as the organohalogenosilane and methanol is employed as ROR'.

6. The process according to claim 3, wherein the Lewis acid is $ZnCl_2$, the organohalogenosilane is dimethyldichlorosilane, ROR' is methanol, and the reaction is effected at a temperature of about 130° to 180° C.

* * * * *